United States Patent [19]

Weber et al.

[11] 4,216,216

[45] Aug. 5, 1980

[54] AROMATIC PIPERAZINYL SUBSTITUTED DIHYDROURACILS

[75] Inventors: Rolf-Ortwin Weber, Wiesbaden-Naurod; Hiristo Anagnostopulos, Taunusstein; Ulrich Gebert, Kelkheim, all of Fed. Rep. of Germany

[73] Assignee: Hoechst Aktiengesellschaft, Frankfurt, Fed. Rep. of Germany

[21] Appl. No.: 915,899

[22] Filed: Jun. 15, 1978

[30] Foreign Application Priority Data

Jun. 18, 1977 [DE] Fed. Rep. of Germany ....... 2727469

[51] Int. Cl.$^2$ .................. A61K 31/505; C07D 403/06
[52] U.S. Cl. .................................... 424/251; 544/295; 544/312; 544/393; 544/396
[58] Field of Search .................. 544/295, 312; 424/251

[56] References Cited

U.S. PATENT DOCUMENTS

| | | | |
|---|---|---|---|
| 2,672,460 | 3/1954 | Conroy | 544/295 |
| 3,466,280 | 9/1969 | Loux | 544/295 |
| 4,100,282 | 7/1978 | Renth et al. | 544/295 |

*Primary Examiner*—Paul M. Coughlan, Jr.

*Attorney, Agent, or Firm*—Quaintance, Murphy & Richardson

[57] ABSTRACT

Compounds of general formula

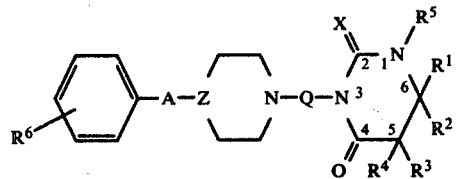

are disclosed wherein appropriate substituents for $R^1$, $R^2$ to $R^5$, $R^6$, A, Q, X, and Z are defined for these novel hexahydropyrimidines. Procedures for the preparation of these compounds are also given. Because of the highly effective serotonin antagonistic activity in combination with a strong inhibiting effect on thrombocyte aggregation and good compatibility these compounds are effective in treating migraine. Additionally, the compounds also exhibit an anti-histamine activity, cause an increase in erythrocyte fluidity, a psychotropic activity, a weak bradykinin antagonism and hypotensive effects.

7 Claims, 21 Drawing Figures

AROMATIC PIPERAZINYL SUBSTITUTED DIHYDROURACILS

This invention relates to novel hexahydropyrimidines and salts thereof, processes for their preparation and to pharmaceutical compositions containing them.

1-(3-Trifluoromethylphenyl)-4-ethyl- or -propylpiperazines in which the alkyl moiety is ω-substituted have been described as having anorectic properties. Substituents in the ω-position of the alkyl moiety which have been described include a 2,4-dioxo-3-hexahydropyrimidinyl group (but without 5- and/or 6- substituents), however, such compounds have not been specifically disclosed.

Pizotyline and methysergide are used as anti-migraine agents because of their serotonin-antagonistic activities. Reports have recently been made of successive migraine treatment being the vascular therapeutic agent Bencyclane which, in addition to exhibiting weak serotonin antagonism, has in particular the property of inhibiting thrombocyte aggregation.

Figure 1:
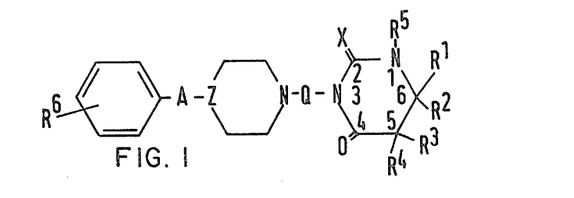
FIG. 1 is Formula I.

According to one aspect of the present invention there are provided compounds of general formula

(I)

wherein $R^1$ represents a hydrogen atom, an alkyl group having 1 or 2 carbon atoms, or a phenyl or tolyl group;

$R^2$ to $R^5$, which may be the same or different, each represents a hydrogen atom or an alkyl group having 1 or 2 carbon atoms;

$R^6$ represents a hydrogen atom, an anellated benzene nucleus or 1 to 3 identical or different substituents selected from the group consisting of alkoxy groups having from 1 to 3 carbon atoms, halogen atoms, nitro or hydroxy groups and alkyl groups having from 1 to 4 carbon atoms optionally substituted by one or more halogen atoms;

A represents a single bond or a

Q represents a single bond or a straight-chained or branched alkylene group of formula $-C_nH_{2n}-$ (in which n is from 2 to 6), at least two carbon atoms being between the two nitrogen atoms to which Q is attached and optionally substituted by not more than (n-2) hydroxy groups in a position other than geminal relative to the two nitrogen atoms to which Q is attached;

X is an oxygen or sulphur atom; and

Z is a nitrogen or a group and acid addition salts thereof.

Compounds of general formula I according to the present invention exhibit interesting pharmacological properties, in particular we have found the compounds to exhibit a highly effective serotonin antagonistic activity in combination with a strong inhibiting effect on thrombocyte aggregation and good compatibility. Thus, the compounds according to the invention are to be considered in the treatment of migraine.

In addition to the above-mentioned pharmacological properties, we have found that the compounds according to the invention also exhibit an anti-histamine activity, cause an increase in erythrocyte fluidity, partly also a psychotropic activity, a weak bradykinin antagonism and hypotensive effects.

It will be appreciated that acid addition salts of the compounds according to the invention for use in medicine should be physiologically acceptable acid addition salts. Other acid addition salts may however be useful in the preparation of the compounds according to the invention or of physiologically acceptable acid addition salts thereof.

Of especial interest by virtue of their favourable properties are compounds of formula I and acid addition salts thereof in which $R^1$ represents an alkyl group having 1 or 2 carbon atoms;

$R^2$ and $R^3$, which may be the same or different, each represents a hydrogen atom or an alkyl group having 1 or 2 carbon atoms;

$R^4$ and $R^5$ each represents a hydrogen atom;

$R^6$ represents a hydrogen or halogen atom, or a halogenoalkyl group having 1 or 2 carbon atoms and up to 3 halogen, preferably fluorine, atoms; p A represents a single bond;

Q represents a straight-chained alkylene group having 2 or 3 carbon atoms;

X represents an oxygen or sulphur atom; and

Z represents a nitrogen atom.

Especially preferred of these compounds are those in which $R^1$ represents a methyl group, one of $R^2$ and $R^3$ represents a methyl group and the other a hydrogen atom and $R^6$ represents a hydrogen atom or a fluorine atom in the 4-position, (such as the compounds numbered 9, 11 and 16 to 18 in the following Table IV).

When halogen atoms are present in the compounds according to the present invention these are preferably selected from fluorine, chlorine, bromine and iodine atoms.

Further preferred compounds according to the invention are those in which $R^6$ represents a $-CF_3$ group in the 3-position, and one of $R^1$ to $R^5$ is other than a hydrogen atom, A represents a Q represents a single bond or is a group having at least 4 carbon atoms, X represents a sulphur atom or Z represents a group

Examples of the group present in the compounds according to the invention are phenyl; 2-, 3- or 4-tolyl; 2,6- or 3,4-dimethylphenyl; 2-, 3- or 4-methoxyphenyl; naphthyl; fluorophenyl; chlorophenyl; bromophenyl; trifluoromethylphenyl and diphenylmethyl groups.

Examples of the group present in the compounds according to the invention are 5,6- or 6,6-dimethyl-5,6-dihydrouracil-3-yl; 5,6- or 6,6-dimethyl-2-thio-5,6-dihydrouracil-3-yl; 1,6,6-trimethyl-2-thio-5,6-dihydrouracil-3-yl; 1,6,6-trimethyl-5,6-dihydrouracil-3-yl; 6-phenyl-5,6-dihydrouracil-3-yl; 6-methyl-5,6-dihydrouracil-3-yl and 5,6-dihydrouracil-3-yl groups.

Examples of the bridging group Q in the compounds according to the invention are, apart from a single bond, ethylene, propylene, butylene, pentylene, hexylene, 2-hydroxypropylene or -butylene groups, which groups with at least 3 carbon atoms may also be branched, so that at least 2 carbon atoms are present in the chain. Any hydroxy groups present should be in positions other than geminally relative to the nitrogen atoms to which Q is attached.

Particularly preferred compounds according to the invention by virtue of their especially favourable properties are the following:

3-{3-[4-(4-fluorophenyl)-1-piperazinyl]-propyl}-6,6-dimethyl-5,6-dihydrouracil hydrochloride hydrate;

3-[3-(4-phenyl-1-piperazinyl)-propyl]-6,6-dimethyl-2-thio-5,6-dihydrouracil hydrochloride;

3-[3-(4-phenyl-1-piperazinyl)-propyl]-6,6-dimethyl-2-thio-5,6-dihydrouracil hydrochloride;

3-[2-(4-phenyl-1-piperazinyl)-ethyl]-6,6-dimethyl-5,6-dihydrouracil hydrochloride; and

3-[2-(4-phenyl-1-piperazinyl)-ethyl]-6,6-dimethyl-2-thio-5,6-dihydrouracil hydrochloride.

Figure 2:
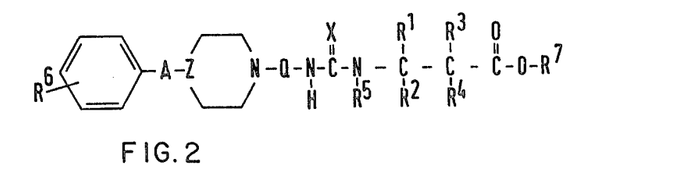
FIG. 2 is Formula II.

Compounds according to the present invention may be prepared by either of the following processes, which processes are further aspects of the present invention: (I) cyclising a compound of formula

Figure 3:
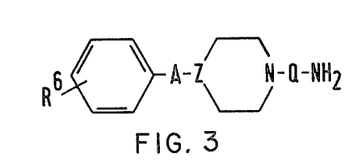
FIG. 3 is Formula III.
Figure 4:
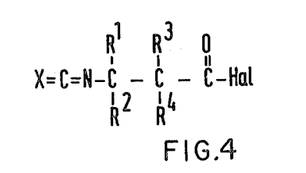
FIG. 4 is Formula IV.
Figure 4A:
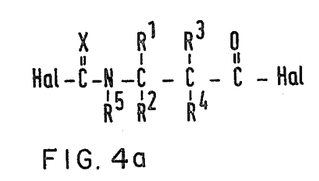

(wherein $R^1$ to $R^6$, A,Q,X and Z are as hereinbefore defined, and $R^7$ represents a hydrogen atom or an alkyl group having from 1 to 4 carbon atoms) with elimination of $R^7OH$; and (II) reacting a compound of formula (wherein $R^6$, A,Q and Z are as hereinbefore defined) with a 3-isocyanato- or 3-isothiocyanato-alkanocarboxylic acid halide of formula (wherein $R^1$ to $R^4$ and X are as hereinbefore defined, and Hal represents a halogen, preferably a chlorine atom) or with a dihalide of formula (wherein $R^1$ to $R^5$, X and Hal are as hereinbefore defined) under deliberation of hydrogen halide.

Cyclisation according to process (a) may be effected under the conditions of conventional condensation methods. For example, it may preferably be carried out in a solvent and/or in the presence of mineral acids and/or by heating the pure starting material of formula II or by heating the reaction mixture obtained from synthesising the compound of formula II in situ, Compounds of formula II in which $R^7$ represents a hydrogen atom may be cyclised especially well in the presence of mineral acids such as, for example sulphuric acid and hydrohalic acids, and preferably hydrochloric or hydrobromic acid, in a solvent comprising an alcohol such as, for example, methanol, ethanol, propanol or isopropanol. However, the reaction may be effected most preferably by heating the pure starting material of formula II in which $R^7$ is hydrogen with the elimination of water with or without solvent and acid, but in the presence of a suitable dehydrating agent such as, for example, acetyl chloride or acetic acid anhydride. The reaction is advantageously carried out at the boiling point of the solvent or condensation agent used.

Cyclisation of compounds of formula II in which $R^7$ is alkyl is preferably carried out in the presence of a solvent and/or mineral acids, e.g. the above-mentioned alcohols and acids.

When the compound of formula II is one in which X is sulphur, cyclising is especially preferred in the presence of a solvent but without the addition of mineral acids. It is also possible to first hydrolyse a compound of formula II in which $R^7$ represents an alkyl group having up to 4 carbon atoms with an alkali metal hydroxide to form a compound of formula II in which $R^7$ represents hydrogen and subsequently to cyclise the latter. Such hydrolysis may be advantageously carried out in aqueous solution or in aqueous-acetone or an aqueous-alcoholic medium. In the latter case the alcohol is conveniently one having 1 to 3 carbon atoms.

Reaction of halides of formula IV and/or IVa is advantageously effected in solvents which are inert under the reaction conditions, such as, for example, methylene chloride, chloroform, toluene and xylene, and preferably in the presence of a tertiary amine such as, for example, triethylamine, tributylamine and pyridine. If desired the reaction may alternatively be effected in pure tertiary amine or in a strongly polar aprotic solvent such as, for example, dimethylformamide. Cooling is advantageously effected at the start of the reaction and heating to the boiling point of the reaction mixture towards the end.

Figure 5:
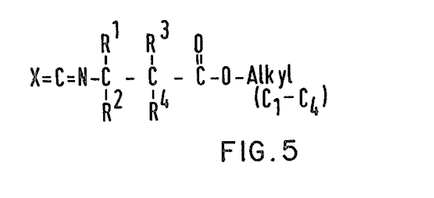
FIG. 5 is Formula V.

The compounds of formula II for use in process (I) according to the invention may be obtained according to the following processes:

(a) (for the preparation of compounds of formula II in which $R^5$ represents a hydrogen atom) reacting an amine of formula III as hereinbefore defined with a 3-isocyanato- or 3-isothiocyanato-alkanocarboxylic acid of formula (V)

(wherein $R^1$ to $R^4$, X are as hereinbefore defined and Alk represents a $C_{1-4}$ alkyl group), and (for the preparation of compounds of formula II in which $R^5$ represents a hydrogen atom or alkyl)

Figure 6:
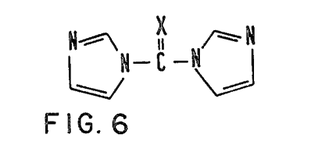
FIG. 6 is Formula VI.

(b) reacting an amine of formula III as hereinbefore defined with a compound of formula (VI)

Figure 7:
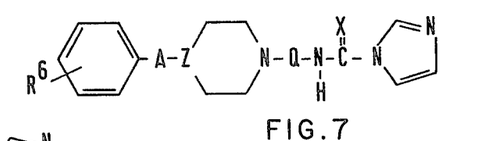
FIG. 7 is Formula VII.

(in which X is as hereinbefore defined) to form an imidazole of formula (VII)

Figure 8:
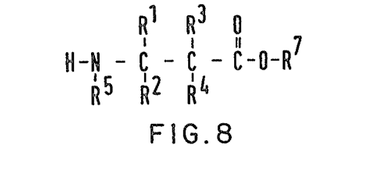
FIG. 8 is Formula VIII.

(in which $R^6$, A, Q, X and Z are as hereinbefore defined) which is subsequently reacted, with or without isolation, with a 3-aminoalkanocarboxylic acid derivative of formula (VIII)

Figure 9:
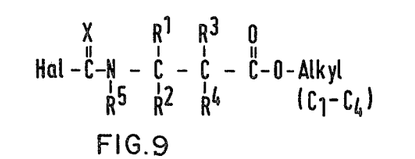
FIG. 9 is Formula IX.
Figure 10X:
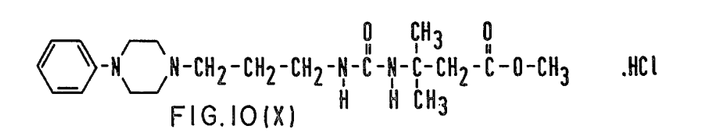
FIG. 10 is Formula X.
Figure 11:
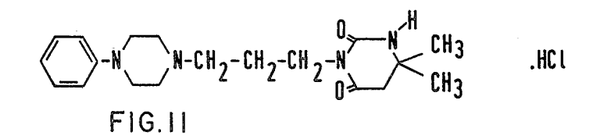
FIG. 11 is Formula XI.
Figure 12:
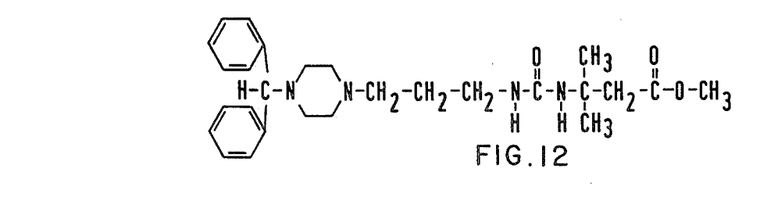
FIG. 12 is Formula XII.
Figure 13:
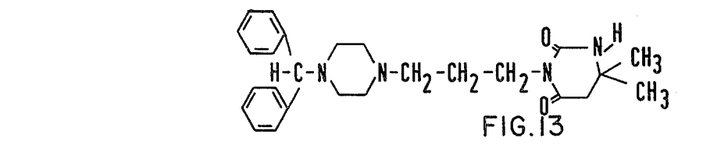
FIG. 13 is Formula XIII.
Figure 14:
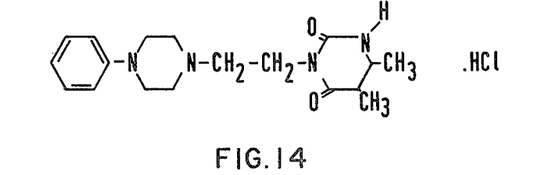
FIG. 14 is Formula XIV.
Figure 15:
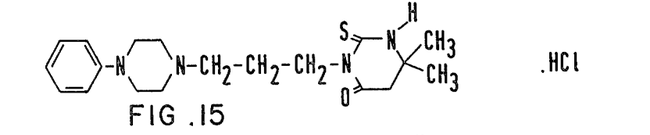
FIG. 15 is Formula XV.
Figure 16:
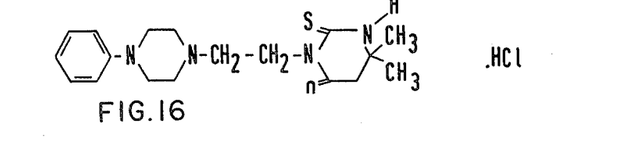
FIG. 16 is Formula XVI.
Figure 17:
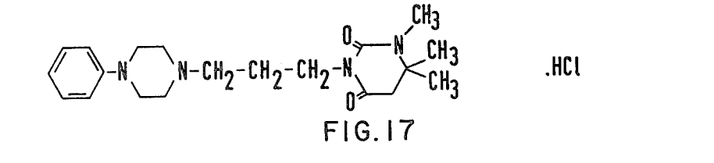
FIG. 17 is Formula XVII.
Figure 18:
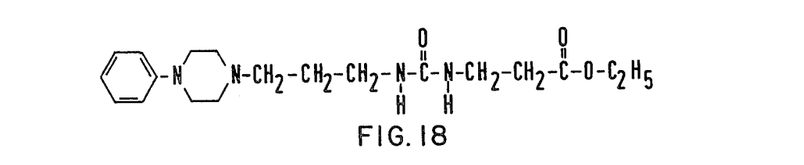
FIG. 18 is Formula XVIII.
Figure 19:
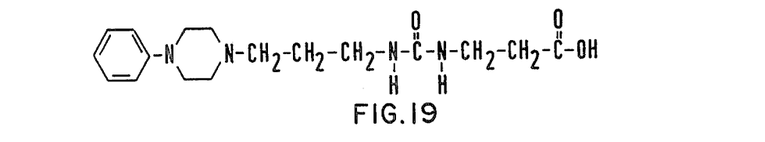
FIG. 19 is Formula XIX.
Figure 20:
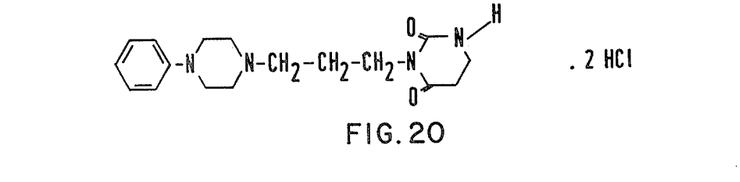
FIG. 20 is Formula XX.

(in which $R^1$ to $R^5$ and $R^7$ are as hereinbefore defined) or an acid addition salt thereof; or (c) reacting an amine of formula III as hereinbefore defined with a carbamoyl halide of formula (IX)

(wherein $R^1$ to $R^5$, X and Hal are as hereinbefore defined and Alk represents a $C_1$–$C_4$ alkyl group).

Starting materials of formula III are, for example, 1-phenyl-4-(3-aminopropyl)-piperazine; 1-(2-methylphenyl)- and 1-(3-methylphenyl)-4-(3-aminopropyl)-piperazine; 1-(2-methoxyphenyl)-, 1-(3-methoxyphenyl)- and 1-(4-methoxyphenyl)-4-(3-aminopropyl)-piperazine; 1-(3,4-dimethylphenyl)- and 1-(2,6-dimethylphenyl)-4-(3-aminopropyl)-piperazine; 1-(3-trifluoromethylphenyl)-, 1-(1-naphthyl)- and 1-(4-fluorophenyl)-4-(3-aminopropyl)-piperazine; 1-phenyl-4-(2-aminoethyl)-piperazine; 1-(2-methoxyphenyl)-4-(2-aminoethyl)-piperazine; 1-(4-methoxyphenyl)-4-(5-aminopentyl)-piperazine; 1-(3-trifluoromethylphenyl)-4-(4-aminobutyl)-piperazine; 1-diphenylmethyl-4-(3-aminopropyl)-piperazine; 4-phenyl-1-(3-aminopropyl)-piperidine; 1-phenyl-4-(4-aminobutyl)-piperazine; 1-phenyl-4-(5-aminopentyl)-piperazine; 1-phenyl-4-aminopiperazine and 4-phenyl-1-(2-aminoethyl)-piperidine.

3-Isocyanato- or isothiocyanato-alkanocarboxylic acid esters of formula V which may be used are, for example, methyl 3-isocyanato-isovalerate and ethyl 3-isocyanatoisovalerate; n- and iso-propyl 3-isocyanato-isovalerate; the various butyl 3-isocyanato-isovalerates; methyl 3-isothiocyanato-isovalerate and ethyl 3-isothiocyanatoisovalerate; n- and iso-propyl 3-isothiocyanato-isovalerate; the various butyl 3-isothiocyanato-isovalerates; methyl 2-methyl-3-isocyanato-butyrate; methyl 2-methyl-3-isothiocyanato-butyrate; methyl 3-phenyl-3-isocyanato-propionate and methyl 3-isocyanato-propionate.

Example of 3-aminoalkanocarboxylic acid derivatives of formula VIII are those which correspond to the above mentioned isocyanato compounds and contain in the 3-position, instead of the isocyanato group, an amino group, such as, for example, methyl 3-aminoisovalerate, methyl 3-amino-2-methylbutyrate, methyl 3-amino-propionate, methyl 3-methylaminoisovalerate, and methyl 3-methylaminoisovalerate.

Process (a) for the preparation of compounds of formula II is advantageously effected in the presence of a solvent which is inert under the reaction conditions such as, for example, xylene, toluene, mesitylene, benzene, methylene chloride or chloroform, and preferably at the boiling point of the solvent used. The reaction may however, also be carried out at room temperature, whereby the reaction mixture generally heats itself. After reaction, the solvent is conveniently removed under reduced pressure and the intermediate compound of formula II may be cyclised either after purification by re-crystallisation or directly as the crude product—as described above—in aqueous solution or in an aqueous-alcoholic medium preferably at its boiling point, and when X in the compound of formula II is oxygen preferably in the presence of mineral acids. When X in the compound of formula II is sulphur, the addition of acid is not generally necessary. The cyclising reaction may also be effected by heating to a temperature of over 150° C., preferably around 200° C. and in the presence of a protective gas.

Process (b) for the preparation of compounds of formula II may be carried out at room temperature and advantageously in the presence of a solvent such as tetrahydrofuran. After addition of the compound of formula VIII, further reaction and the above mentioned cyclising of the product are, however, advantageously carried out at the boiling point of the reaction mixture. Compounds of formula II in which $R^7$ is hydrogen are preferably cyclised by heating in the absence of solvent after they have been isolated in pure form and advantageously at a temperature over 150° C., preferably at approximately 200° C. and in the presence of a protective gas. When compounds of formula VIII which are only sparingly soluble are used in the reaction, it is convenient to add a polar solvent such as dimethylformamide, which is inert to the reaction materials, so that a homogeneous solution is obtained.

The preparation of mono- or bis-acid addition salts is generally carried out by conventional methods. Physiologically acceptable material, organic or sulphonic acids, may be used for this purpose, such as, for example, hydrochloric acid, hydrobromide acid, sulphuric acid, benzosulphonic acid methanesulphonic acid, p-toluenesulphonic acid and cyclohexylsulphamic acid.

According to a further aspect of the present invention there are provided pharmaceutical compositions comprising as active ingredient at least one compound of formula I or a physiologically acceptable acid addition salt thereof in association with a pharmaceutical carrier or excipient. Therein the compounds of formula I which are generally crystalline have a good stability.

The compositions according to the invention may be in a form suitable for oral, rectal or parenteral administration, such as, for example, in the form of tablets, capsules, powders, emulsions, suspensions, granulates, syrups, solutions, suppositories or forms adapted to provide a sustained release of active ingredient.

The compositions according to the invention may be prepared by known methods using carriers or excipients conventional to the pharmaceutical art.

Thus, for example, they may be prepared by admixing suitable and compatible auxiliary agents such as starch, lactose, cellulose derivatives, stearic acid or its salts, solvents; dissolving agents, suppository masses; carriers, such as chlorides, phosphates and carbonates, in a conventional way.

Administration of the pure compounds in the form of microcapsules is also possible, as is a combination with other physiologically active ingredients.

The composition may if desired be administered in dosage unit form. Suitable dosages for humans being for example 0.1 to 50 mg, preferably 0.5 to 10 mg, and most preferably 0.5 to 3 mg per os per day per adult subject.

If desired, the compounds according to the present invention may be used in combination with one or more further physiologically active ingredients, such as, for example, analgesics, ergotamine preparations, other serotonin antagonists, spasmolytics, vasodilating agents, β-symphatholytics, antemetics, anti-histaminic agents, sedatives, tranquilizers, caffeine, nicotine acid derivatives, vitamins and oestrogens.

PHARMACOLOGICAL TESTS AND RESULTS

1. Serotonin-antagonistic activity

For determination of the serotonin-antagonistic activity the following pharmacological tests were used: Test a: (Test according to Konzett and Rössler (Arch. exp. Path. Pharmak. 195 (1940) 71). Domestic albino guinea pigs were anaesthetised with 1.25 g/kg of urethane intraperitoneally (i.p.). Bronchial resistance was recorded in the open thorax by a recorder ("bronchotransducer") manufactured by the firm Ugo Basile (Milan); respiratory frequency was kept constant by artificial respiration at a frequency of 58 strokes/minute, the inflation pressure was 9 cm $H_2O$ column. To induce bronchospasms, 5 to 10 mg/kg of serotonin (as serotonin-creatinine sulphate) were injected into one of the jugular veins every 15 minutes in a volume of 0.1 ml/kg body weight. The test substances were administered in a volume of 1 ml/kg either intravenously within 30 seconds, 2 minutes before generation of the serotonin spasm or intraduodenally or orally by oesphageal tube 15 minutes before the spasm. The $ED_{50}$ value corresponded to the dose by which a serotonin spasm is inhibited by 50% 2 minutes after i.v. injection or 15 minutes after oral or intraduodenal administration of the test substance. The results are given in Table I. Test b: (Serotonin antagonism in the isolated uterus of rats according to Robert A. Turner: Screening Methods in Pharmacology, Academic Press 1965 (New York and London)) Female Sprague-Dawley rats with a weight of 180 to 240 g were given intraperitoneally 2 mg of Oestromon (Merck, Darmstadt) 24 hours before extraction of the uterus in order to induce oestrus. The organ bath was kept at 22° C. and contained a Tyrode solution having a specific composition. The test substance was added to the bath in aqueous solution with a total volume of 0.1 ml. The serotonin concentration administered was $10^{-8}$ g/ml bath. The $ED_{50}$ value corresponded to the dose by which a serotonin spasm is inhibited by 50%. The results are given in Table 1. Test c: (5-Hydroxy-L-tryptophan antagonism in mice). A single administration of 5-hydroxy-L-tryptophan causes in mice a strong increase in defecation due to the increased biosynthesis of serotonin from exogenically supplied amino acids. This defecation effect can be reduced by serotonin antagonists. The test substances were administered orally 45 minutes before administration of the tryptophan. The tryptophan dose was 40 mg/kg i.p.

Evaluation was carried out 1 hour after administration of the preparation by measurement of the quantity of faeces produced. A reduction in this quantity by not more than 25% of the control is indicated, according to the result, by 0 or (+), from 25 to 50% by +, from 50 to 75% by ++ and over 75% +++ (see Table I).

Table I

| Test | Substance no. | Type of administration | ED$_{50}$ in μg/kg | n |
|---|---|---|---|---|
| a | 9 | i.v. | 3–10 | 5 |
| | | i.d. | 10–30 | 3 |
| | | p.o. | 100–300 | 3 |
| | 11 | i.v. | 10–30 | 2 |
| | | i.v. | 10–30 | 3 |
| | 16 | i.d. | 300 | 2 |
| | | p.o. | ca. 300 | 2 |
| | 17 | i.v. | 1–3 | 6 |
| | | i.d. | 10–30 | 2 |
| | 18 | i.v. | 1–3 | 7 |
| | | i.d. | ca. 30 | |
| | Pizotyline-HCl | i.v. | 10–50 | 2 |
| | | i.d. | 10–100 | 2 |
| | | p.o. | 500–1000 | 2 |

| Test | Substance no. | ED$_{50}$ in μg/ml bath | n |
|---|---|---|---|
| b | 9 | 0.001–0.01 | 3 |
| | 16 | 0.001–0.01 | 3 |
| | 17 | 0.001–0.01 | 4 |
| | 18 | 0.0001–0.001 | 4 |
| | Pizotyline-HCl | 0.001–0.01 | 4 |

| Test | Substance no. | Dose in mg/kg p.o. | Strength of activity | n |
|---|---|---|---|---|
| c | 16 | 10 | + | 10 |
| | | 20 | + | 10 |
| | 17 | 10 | + | 10 |
| | | 20 | ++ | 10 |
| | 18 | 10 | ++ | 10 |
| | | 20 | ++ | 10 |
| | Pizotyline-HCl | 20 | + | 30 |

Abbreviations
i.v. = intravenous
i.d. = intraduodenal
p.o. = per os
n = number of animals 2. Thrombocyte aggregation inhibiting activity According to G. V. R. Born, Nature 4832, 927–929 (1962) and K. Breddin et al., Klin, Wschr. 53, 81–89 (1975).

Thrombocyte aggregation was induced experimentally in platelet-rich plasm (PRP) of beagle dogs by in vitro administration of adenosine diphosphate (ADP) in a final concentration of $2.5 \times 10^{-6}$ and was measured by means of a universal aggregometer (manufactured by B. Braun/Melsungen). An Eppendorf Photometer recorded the change in the optical density of the plasma.
The following parameters were determined:
1. The angle, α, between the tangent at the starting point of the curve and the horizontal axis,
2. The time, Tr, from the start of rotation (aggregation) until complete disaggregation,
3. The maximum amplitude (Ma) of the aggregation curve as the difference between starting transmission and maximum transmission.

Table II

| Substance No. | Final concentration in g/ml | α | Tr min | Ma | Change of Ma in % |
|---|---|---|---|---|---|
| 9 | $10^{-5}$ | 86.5 | 4.6 | 535 | −11 |
| (n = 5) | $3 \times 10^{-5}$ | 86.6 | 4.3 | 523 | −13 |
| | $10^{-4}$ | 87.0 | 4.0 | 483 | −20 |
| 16 (n = 5) | $10^{-4}$ | 86.3 | 1.8 | 315 | −42 |
| 17 (n = 5) | $10^{-4}$ | 85.9 | 2.3 | 344 | −18 |

Table II-continued

| Substance No. | Final concentration in g/ml | α | Tr min | Ma | Change of Ma in % |
|---|---|---|---|---|---|
| 18 (n = 5) | $10^{-4}$ | 85.8 | 3.0 | 328 | −19 |
| Fludilate (n = 20) | $10^{-4}$ | 85.2 | 2.6 | 324 | −34 |

3. Acute toxicity

Table III sets out for some compounds, the toxicity determined in mice and rats after intraperitoneal and intravenous administration over the mortality occurring within 7 days as LD$_{50}$ or LD$_{50}$ range.

Table III

| Substance no. | Type of application | LD$_{50}$ in mg/kg* Mice | LD$_{50}$ in mg/kg* Rats |
|---|---|---|---|
| 9 | i.v. | 83 (75.7–91) | 60 (53–67)** |
| | i.p. | 100–300** | |
| 11 | i.p. | 100–300 | |
| 16 | i.v. | 40–63 | |
| | i.p. | 200–400 | |
| 17 | i.v. | 54 (51–57) | 25–40 |
| 18 | i.v. | 100–150 | 66 (63–69) |
| Pizotyline HCl*** | i.v. | 43 ± 1.8 | 17 ± 1.1 |

*Calculated according to Litchfield and Wilcoxon, J. Pharmacol. exp. Ther.96, 99 (1949)
**for the base
***Speigt, T. M. and G. S. Avery, Drugs, 3, 159–203 (1972)

As the above Tables show the compounds according to the invention which we have tested are for the most part superior to the comparative substance Pizotyline HCl. Furthermore, animal-experimental analyses have shown further benefits in comparison with Pizotyline HCl in that (a) the activity occurs substantially more rapidly, (b) no sedation is provoked in the therapeutic dose range and (c) no undesirable stimulation of appetite is caused.

The following Examples serve to illustrate the preparation of compounds according to the present invention:

Example 1:
3-[3-(4-Phenyl-1-piperazinyl)-propyl]-6,6-dimethyl-5,6-dihydrouracil hydrochloride [Table IV, No. 9]

(A) According to process (a) 11.0 g (0.05 mol) of 1-phenyl-4-(3-aminopropyl)-piperazine and 7.85 g (0.05 mol) of methyl 3-isocyanato-isovalerate are each dissolved in 50 ml of toluene, mixed together and heated briefly to boiling point. After cooling, the solvent is distilled off under reduced pressure and the oily residue is dissolved in ether. After the addition of petroleum ether and rubbing with a glass rod the compound of formula II is obtained in crystalline form and can be recrystallised from an acetone-petroleum ether mixture. Melting range 75° to 77° C.; yield 15.1 g (80.0% of theory).

For conversion into the hydrochloride, the base is dissolved in acetone and mixed with an equimolar quantity of N hydrochloric acid. The solvent is removed under reduced pressure at 30° C. maximum and the residue is re-crystallised from dioxane. The intermediate product methyl 3-{3-[3-(4-phenyl-1-piperazinyl)-propyl]ureido}-isovalerate hydrochloride is obtained in pure form. Yield; quantitative; melting range 168° to 170° C.; $C_{20}H_{33}ClN_4O_3$; molecular weight 412.96.

Analysis: Calculated: C 58.17; H 8.05; N 13.57. Found: C 58.07; H 7.97; N 13.46.

For cyclisation, the compound is dissolved in approximately 10 times its quantity of 12% hydrochloric acid and refluxed for 2 hours, during the last hour approximately half the solvent is distilled off at normal pressure. The resulting mixture is evaporated under reduced pressure, the residue is dissolved in water and an excess of aqueous sodium hydroxide solution is added. The precipitated base is taken up in methylene chloride, dried over sodium sulphate and re-crystallised after evaporation from a mixture of methanol and diisopropyl ether. Melting range 135° to 136° C. Cyclising may also be effected by heating 5.65 g (0.015 mol) of methyl 3-{3-[3-(4-phenyl-1-piperazinyl)-propyl]ureido}isovalerate to 200° C. for approximately 1.5 hours under a nitrogen atmosphere.

The progress of the reaction is followed by thin-layer chromatography. On completion of the reaction the solidified molten mass is rubbed with diisopropyl ether, purified over a chromatography column and re-crystallised from methanol and diisopropyl ether. Yield: 2.5 g (48% of theory); melting range: 134° to 136° C.

To convert into the corresponding monohydrochloride, the base is dissolved in methanol and mixed with the calculated quantity of N hydrochloric acid. After evaporation under reduced pressure the residue is re-crystallised from methanol or water. Melting range 236° to 242° C.; formula $C_{19}H_{29}ClN_4O_2$; molecular weight: 380.92.

Analysis: Calculated: C 59.91; H 7.67; Cl 9.31; N 14.71. Found: C 60.28; H 7.75; Cl 9.39; N 14.73.

(b) The same substance may also be prepared as follows: According to process (a) a solution of 21.9 g (0.1 mol) of 1-phenyl-4-(3-aminopropyl)-piperazine in 100 ml of toluene is mixed with stirring with a mixture of 15.7 g (0.1 mol) of methyl 3-isocyanato-isovalerate and 100 ml of toluene. The mixture is heated briefly to boiling point, cooled to room temperature, evaporated to dryness and the residue dissolved in approximately 1 liter of acetone. After the addition of 100 ml (0.1 mol) of N sodium hydroxide solution the reaction mixture is stirred at room temperature for approximately 20 hours. 100 ml (0.1 mol) of N hydrochloric acid are then added, evaporated to dryness, the residue re-crystallised from a mixture of acetone and petroleum ether and the free 3-{3-[3-(4-phenyl-1-piperazinyl)-propyl]-ureido{isovaleric acid is obtained as an intermediate. Yield: 23.9 g (66% of theory); melting range: 139° to 140° C.; formula: $C_{19}H_{30}N_4O_3$; molecular weight 362.47.

Analysis: Calculated: C 62.96; H 8.34; N 15.46. Found: C 62.93; H 8.30; N 15.30. The intermediate thus obtained is heated for approximately 1 hour to 180°–200° C. After cooling the solidified base is purified by column chromatography and re-crystallised from a mixture of methanol and diisopropyl ether. Melting range: 135°–136° C.

An alternative cyclisation reaction of the open-chained carboxylic acid into the corresponding 5,6-dihydrouracil may be carried out by heating the acid for 2 hours in aqueous-alcoholic hydrochloric acid, acetyl chloride or acetic acid anhydride. After removal of the corresponding condensation agent (dehydrating agent) under reduced pressure the residue is dissolved in water and mixed with excess potassium hydroxide solution. The precipitated base is dissolved in methylene chloride, dried over sodium sulphate and after evaporation of the solvent purified optionally by column chromatography.

Example 2:
3-[3(4-Diphenylmethyl-1-piperazinyl)-propyl]-6,6-dimethyl-5,6-dihydrouracil [Table IV, No. 30]

9.0 g (0.029 mol) of 1-diphenylmethyl-4-(3-aminopropyl)-piperazine are dissolved in 30 ml of toluene and according to process alternative (a) mixed with stirring with a mixture of 4.6 g (0.029 mol) of methyl 3-isocyanatoisovalerate and 20 ml of toluene. The mixture is heated for 30 minutes to approximately 70° C., evaporated to dryness under reduced pressure and the oily residue rubbed after the addition of diethyl ether. The methyl 3-(1-diphenylmethylpiperazin-4-ylpropylureido)-isovalerate thus obtained is pure according to its thin-layer chromatogram.

Yield: 9.8 g (72% of theory).

9.8 g (0.021 mol) of the ester isolated are dissolved in about 150 ml of methanol, mixed with 30 ml of concentrated hydrochloric acid and refluxed for 2 hours. After removal of the solvent under reduced pressure, the oily residue is dissolved in water and the base released with aqueous potassium hydroxide solution. The mixture is shaken with chloroform, the organic phase dried over sodium sulphate and evaporated. The crystalline residue is washed several times with ether.

Yield: 7.1 g (77.8% of theory). Melting range: 183°–185° C. Formula: $C_{26}H_{34}N_4O_2$. Molecular weight: 434.58.

Analysis: Calculated C 71.86; H 7.89; N 12.89. Found: C 71.85; H 8.05; N 13.02.

The compound can subsequently be converted into desired acid addition salts by the conventional methods.

Example 3:
3-[2-(4-Phenyl-1-piperazinyl)-ethyl]-5,6-dimethyl-5,6-dihydrouracil hydrochloride [Table IV, No. 22]

According to process alternative (a) 20.5 g (0.1 mol) of 1-phenyl-4-(2-aminoethyl)-piperazine and 15.7 g (0.1 mol) of methyl 3-isocyanato-2-methyl butyrate are each dissolved in 125 ml of toluene, mixed together at room temperature and refluxed for 5 minutes. The mixture is evaporated under reduced pressure, mixed with 200 ml of 3 N hydrochloric acid and boiled for approximately 1 hour. Towards the end of the reaction time approximately half the hydrochloric acid is distilled off at atmospheric pressure; the rest is subsequently removed under reduced pressure. The residue crystallises after rubbing in methanol and is re-crystallised several times from methanol-water. Yield: 21.5 g (58.7% of theory); melting range: 265° to 273° C.; formula $C_{18}H_{27}ClN_4O_2$; molecular weight: 366.89.

Analysis: Calculated: C 58.93; H 7.42; Cl 9.66; N 15.27. Found: C 58.73; H 7.53; Cl 9.70; N 15.16.

Example 4:
3-[3-(4-Phenyl-1-piperazinyl)-propyl]-6,6-dimethyl-2-thio-5,6-dihydrouracil hydrochloride [Table IV, No. 16]

According to process alternative (a) a solution of 21.9 g (0.1 mol) of 1-phenyl-4-(3-aminopropyl)-piperazine in 100 ml of toluene is mixed with stirring with a mixture of 17.3 g (0.1 mol) of methyl 3-isothiocyanato-isovalerate and 100 ml of toluene. The reaction mixture is refluxed for 15 minutes and subsequently the solvent is evaporated off under reduced pressure. The evaporation residue is purified on a silica gel 60 column (E. Merck) diameter: 6 cm, height: 70 cm) with a chloroform-methanol mixture (volume ratio 9:1).

Yield: 19.1 g (53% of theory). Melting range: 150°–151° C.

For conversion into the hydrochloride salt, the previously obtained 19.1 g of base are dissolved in methanol and mixed with 53 ml of N hydrochloric acid. After evaporation a solid crystalline residue is obtained which can be re-crystallised from methanol. Melting range: 200°–217° C.; formula: $C_{19}H_{29}ClN_4OS$; molecular weight: 396.98.

Analysis: Calculated: C 57.49; H 7.36; Cl 8.93; N 14.11; S 8.08 Found: C 57.71; H 7.46; Cl 8.96; N 14.10; S 8.22

EXAMPLE 5:
3-[2-(4-Phenyl-1-piperazinyl)-ethyl]-6,6-dimethyl-2-thio-5,6-dihydrouracil hydrochloride [Table IV, No. 18]

According to process alternative (b) to a solution of 25.8 g (0.15 mol) of N,N'-thiocarbonyl-diimidazole in 500 ml of anhydrous tetrahydrofuran is added dropwise 29.8 g (0.15 mol) of 1-phenyl-4-(2-aminoethyl)-piperazine in 125 ml of anhydrous tetrahydrofuran over 90 minutes with stirring. The mixture is stirred for 30 minutes and, with stirring, 24.3 g (0.15 mol) of anhydrous methyl 3-aminoisovalerate hydrochloride are subsequently added. The clear solution is refluxed for 120 minutes. After cooling to room temperature a solution of 3.33 g (0.145 gram atom) of sodium in 200 ml of methanol is added and stirred for 15 minutes. The solvent is removed under reduced pressure and the crystalline residue is washed several times with water. After drying, the base is washed with diethyl ether and re-crystallised from ethanol. Yield: 35.7 g (71% of theory); melting range: 185°–188° C.

To prepare the monohydrochloride, the base is dissolved in methylene chloride and mixed with an excess of ethanolic hydrochloric acid. After the addition of diethyl ether a colourless crystalline substance is obtained which is re-crystallised twice from ethanol and is the monohydrochloride. The pH value of a 0.1% aqueous solution lies at about 4.3. Melting range 239° to 240° C.; formula: $C_{18}H_{27}ClN_4OS$; molecular weight: 382.95.

Analysis: Calculated: C 56.46; H 7.11; Cl 9.26; N 14.63; S 8.37. Found: C 56.48; H 7.11; Cl 9.60; N 14.62; S 8.67.

To prepare the dihydrochloride hydrate, the base is dissolved in methanol containing a little water and mixed with an excess of alcoholic hydrochloric acid.

After precipitation with diethyl ether the desired compound is obtained which has any remaining hydrochloric acid evaporated off under reduced pressure at room temperature and is then dried over calcium chloride. The pH value of a 10% aqueous solution lies around 1.8. Melting range: 238° to 247° C. with decomposition: formula: $C_{18}H_{30}Cl_2N_4O_2S$; molecular weight: 437.42.

Analysis: Calculated: C 49.43; H 6.91; Cl 16.21; N 12.81; S 7.33. Found: C 49.94; H 6.95; Cl 16.71; N 12.90; S 7.35.

EXAMPLE 6:
3-[3-(4-Phenyl-1-piperazinyl)-propyl]-1,6,6-trimethyl-5,6-dihydrouracil hydrochloride [Table IV, No. 26]

According to process alternative (b) to a solution of 16.2 g (0.1 mol) of N,N'-carbonyldiimidazole in 500 ml of anhydrous tetrahydrofuran is added dropwise 21.9 g (0.1 mol) of 1-phenyl-4-(3-aminopropyl)-piperazine in 150 ml of anhydrous tetrahydrofuran over 90 minutes with stirring. The mixture is stirred for 30 minutes and, with stirring, 18.1 g (0.1 mol) of methyl 3-methyaminoisovalerate hydrochloride and 100 ml of anhydrous dimethylformamide are added. After refluxing for 180 minutes, the solution is cooled to room temperature, a solution of 2.29 g (0.1 gram atom) of sodium in 50 ml of methanol is added and stirred for a further 15 minutes. After removal of the solvent under reduced pressure the oily residue is dissolved in diethyl ether. Undissolved solids are filtered off, the ether solution is evaporated under reduced pressure and the residue is mixed with a little methanol, so that the desired base is precipitated in crystalline form. The compound may be re-crystallised from methanol. Yield: 24.7 g (68.9% of theory).

To convert to the hydrochloride, the base is dissolved in acetone and mixed with an equivalent quantity of N hydrochloric acid. After evaporation under reduced pressure the crystalline residue is re-crystallised from methanol with diethyl ether. The pH value of a 0.1% solution lies around 3.0. Melting range: 188°–195° C.; formula: $C_{20}H_{31}ClN_4O_2$; molecular weight: 394.94.

(XVII)

Analysis: Calculated: C 60.82; H 7.91; Cl 8.98; N 14.19. Found: C 60.39; H 7.87; Cl 9.80; N 13.69.

EXAMPLE 7:
3-[3-(4-Phenyl-1-piperazinyl)-propyl]-5,6-dihydrouracil dihydrochloride [Table IV, No. 32]

According to process alternative (a) 21.9 g (0.1 mol) of ethyl 3-isocyanato-propionate and 14.3 g (0.1 mol) of 1-phenyl-4-(3-aminopropyl)-piperazine are each dissolved in 100 ml of toluene, mixed together and briefly heated to boiling. After evaporation the residue is rubbed in diethyl ether, washed and re-crystallised from diethyl ether to obtain ethyl-3-{3-[3-(4-phenyl-1-piperazinyl)-propyl]-ureido}propionate. Yield 19.2 g (53% of theory) (a further fraction of the desired product can be isolated from the mother liquor). Melting range: 66° to 69° C.

(XVIII)

19.0 g (0.0524 mol) of this ester are dissolved in 250 ml of acetone and mixed with 52.4 ml of N sodium hydroxide solution. The mixture is stirred at room temperature for 18 hours, 52.4 ml of N hydrochloric acid are added, the mixture is evaporated and the residue is re-crystallised from methanol, to yield 3-{3-[3-(4-phenyl-1-piperazinyl)-propyl]-ureido}propionic acid. Yield: 15.9 g (90% of theory). Melting range: 169°–171° C.

(XIX)

2.5 g of 3-{3-[3-(4-phenyl-1-piperazinyl)-propyl]-ureido}propionic acid are refluxed in 35 ml of acetic acid anhydride for approximately 2 hours. The mixture is evaporated, the residue is dissolved in diethyl ether and the whole is again dissolved in methanol. After the addition of ethereal hydrochloric acid, a crystalline precipitate is obtained which is isolated and subsequently boiled in ethanol until no more acetyl derivative can be detected by thin-layer chromatography. The compound is then re-crystallised from methanol.

Yield: 1.5 g (51.5% of theory). Melting range: 192°–216° C. with decomposition. Formula: $C_{17}H_{26}Cl_2N_4O_2$. Molecular weight: 389.32.

(XX)

Analysis: Calculated: C 52.45; H 6.73; Cl 18.21; N 14.39. Found: C 52.48; H 6.84; Cl 18.37; N 14.56. The following Table IV gives details of further Examples of compounds according to the present invention.

Table IV

| No. | Product | Melting range °C. (+) | Preparation to Example |
|---|---|---|---|
| 1 | 3-[3-(4-(3-Methylphenyl)-1-piperazinyl)-propyl]-6,6-dimethyl-5,6-dihydrouracil-hydrochloride | 93–197° (122–125°) | 2 |
| 2 | 3-[3-(4-(2-Methoxyphenyl)-1-piperazinyl)-propyl]-6,6-dimethyl-5,6-dihydrouracil-hydrochloride | 215–230° (122–123°) | 2 |
| 3 | 3-(4-Fluorophenyl)-1-piperizinyl)-propyl]3-(4-(2-Methylphenyl)-1-piperazinyl)-propyl]-6,6-dimethyl-5,6-dihydrouracil-hydrochloride | 235–270° (116–118°) | 2 |
| 4 | 3-[3-(4-(3-Methoxyphenyl)-1-piperazinyl)-propyl]-6,6-dimethyl-5,6-dihydrouracil-hydrochloride | 175–178° (92–94°) | 2 |
| 5 | 2-[3-(4-Methoxyphenyl)-1-piperazinyl)-propyl]3-(4-Methoxyphenyl)-1-piperazinyl)-propyl]-6-6-dimethyl-5,6-dihydrouracil-hydrochloride | 233–240° (163–167°) | 2 |
| 6 | 3-[3-(4-(3,4-Dimethylphenyl)-1-piperazinyl)-propyl]-6,6-dimethyl-5,6-dihydrouracil-hydrochloride | 230–240° (162–163°) | 2 |
| 7 | 3-[3-(4-(2,6-Dimethylphenyl)-1-piperazinyl-propyl]-1-piperazinyl-propyl]-6,6-dimethyl-5,6-dihydrouracil-hydrochloride | 243–260° (121–125°) | 2 |
| 8 | 3-[3-(4-(3-Trifluormethylphenyl)-1-piperazinyl)-propyl]-6,6-dimethyl-5,6-dihydrouracil-hydrochloride | 240–245° (108–109°) | 2 |
| 9 | 3-[3-(4-Phenyl-1-piperazinyl)-propyl]-6,6-dimethyl-5,6-dihydrouracil-hydrochloride | 236–242° (135–136°) | 1,7 |
| 10 | 3-[3-(4-Naphthyl)-1-piperazinyl)-propyl]-6,6-dimethyl-5,6-dihydrouracil-hydrochloride | 265–285° | 2 |
| 11 | 3-[3-(4-Fluorphenyl)-1-piperazinyl)-propyl]-6,6-dimethyl-5,6-dihydrouracil-hydrochloride hydrate | 198–200° (140–141°) | 2 |
| 12 | 3-[2-(4-Phenyl-1-piperazinyl)-ethyl]-6,6-dimethyl-5,6-dihydrouracil-hydrochloride | 240–256° (140–144°) | 2 |
| 13 | 3-[2-(4-(2-Methoxyphenyl-1-piperazinyl)-ethyl]-6,6-dimethyl-5,6-dihydrouracil-hydrochloride | 230–242° | |
| 14 | 3-[5-(4-(4-Methoxyphenyl)-1-piperazinyl)-pentyl]-6,6-dimethyl-5,6-dihydrouracil-hydrochloride 1,5 H₂O | 153–157° | 3 |
| 15 | 3-[4-(3-Trifluormethylphenyl)-1-piperazinyl)-butyl]-6,6-dimethyl-5,6-dihydrouracil-hydrochloride | 205–214° | 3 |
| 16 | 3-[3-(4-Phenyl-1-piperazinyl)-propyl]-6,6-dimethyl-2-thio-5,6-dihydrouracil-hydrochloride | 200–217° (150–151°) | 4 |
| 17 | 3-[3-(4-Phenyl-1-piperazinyl)-propyl]-5,6-dimethyl-5,6-dihydrouracil-hydrochloride | 216–227° | 2 |
| 18 | 3-[2-(4-Phenyl-1-piperazinyl)-ethyl]-6,6-dimethyl-2-thio-5,6-dihydrouracil-hydrochloride | 239–240° (185–188°) | 5 |
| 19 | 3-[4-(4-Phenyl-1-piperazinyl)-butyl]-6,6-dimethyl-5,6-dihydrouracil-hydrochlorid-hydrate | 204–216° (145–147°) | |
| 20 | 3-[5-(4-Phenyl-1-piperazinyl)-pentyl]-5,6-dimethyl-5,6-dihydrouracil-hydrochloride | 198–204° | 2 |
| 21 | 3-[5-(4-phenyl-1-piperazinyl)-pentyl]-6,6-dimethyl-5,6-dihydrouracil-hydrochloride | 187–193° (109–110°) | 2 |
| 22 | 3-[2-(4-Phenyl-1-piperazinyl)-ethyl]-5,6-dimethyl-5,6-dihydrouracil-hydrochloride | 265–273° | 3 |
| 23 | 3-[2-(4-Phenyl-1-piperazinyl)-ethyl]-5,6-dimethyl-2-thio-5,6-dihydrouracil-hydrochloride | 244–250° | 5 |
| 24 | 3-(4-Phenyl-1-piperazinyl)-6,6-dimethyl-5,6-dihydrouracil-hydrochlorid-hydrate | 214–217° | 3 |
| 25 | 3-[2-(4-Phenyl-1-piperazinyl)-ethyl]-1,6,6-trimethyl-2-thio-5,6-dihydrouracil-dihydrochloride | 183–186° | 6 |
| 26 | 3-[3-(4-Phenyl-1-piperazinyl)-propyl]-1,6,6-trimethyl-5,6-dihydrouracil-hydrochloride | 188–195° | 6 |
| 27 | 3-[3-(4-Phenyl-1-piperazinyl)-propyl]-6-phenyl-5,6-dihydrouracil-hydrochloride | 115–120° | 3 |
| 28 | 3-[3-(4-Phenyl-1-piperazinyl)-propyl]-6,6-dimethyl-5,6-dihydrouracil-hydrochloride | 207–210° (125–126°) | 3 |
| 29 | 3-[3-(4-Phenyl-1-piperazinyl)-propyl]-5,6-dimethyl-5,6-dihydrouracil-hydrochloride | 223–238° (183–185°) | 3 |
| 30 | 3-[3-(4-Diphenylmethyl-1-piperazinyl)-propyl]-6,6-dimethyl-5,6-hydrouracile | 195–196° | 2 |
| 31 | 3-[3-(4-Diphenylmethyl-1-piperazinyl)-propyl]-5,6-dimethyl-5,6-dihydrouracile | 192–216° with decomp. | 2 |
| 32 | 3-[3-(4-Phenyl-1-piperazinyl)-propyl]-5,6-dihydrouracil-dihydrochloride | | |
| 33 | 3-[3-(4-Phenyl-1-piperazinyl)-2-hydroxypropyl]-5,6-dihydrouracil-hydrochloride | 220–234° with decomp. | 1 |

(+)The melting ranges were determined with a Kofler heating bench and are uncorrected. The melting ranges of the corresponding bases are given in parentheses.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:
1. Compounds of formula wherein $R^1$ represents a radical selected from the group consisting of hydrogen, phenyl, tolyl or alkyl having at most 2 carbon atoms;

$R^2$ to $R^5$ each represent hydrogen or alkyl having at most 2 carbon atoms;

$R^6$ represents a radical selected from the group consisting of hydrogen, anellated benzene nucleus, 1 to 3 identical or different substituents selected from the group consisting of alkoxy groups having from 1 to 3 carbon atoms, halogen atoms, nitro and hydroxy groups, alkyl groups having from 1 to 4 carbon atoms and such alkyl group being substituted by at least one halogen atom;

A represents a single bond or a $$C_6H_5-\overset{/}{\underset{\backslash}{C}H} \text{ group};$$

Q represents a radical selected from the group consisting of single bond, straight-chained or branched alkylene group of formula $-C_nH_{2n}-$ in which n is from 2 to 6, at least two carbon atoms being between the two nitrogen atoms to which Q is attached and such an alkylene group; being substituted by not more than (n-2) hydroxy groups which are bound to a carbon atom not being linked to one of the nitrogen atoms to which Q is attached;

X is oxygen or sulphur atom; and

Z is nitrogen or the group $$-\overset{/}{\underset{\backslash}{C}H}$$

and acid addition salts thereof.

2. Compounds as claimed in claim 1 in which
$R^1$ represents alkyl having at most 2 carbon atoms;
$R^2$ and $R^3$ each represent hydrogen or alkyl having at most 2 carbon atoms;
$R^4$ and $R^5$ each represent hydrogen atom;
$R^6$ represents a radical selected from the group consisting of hydrogen, halogen, and halogenalkyl having at most 2 carbon atoms and up to 3 halogen atoms;
A represents single bond;
Q represents straight-chained alkylene group having 2 to 3 carbon atoms;
X represents oxygen or sulphur; and
Z represents nitrogen atom.

3. Compounds as claimed in claim 1 wherein $R^1$ represents methyl; one of $R^2$ and $R^3$ represents methyl group and the other hydrogen atom; and $R^6$ represents hydrogen atom or fluorine atom in the 4-position.

4. Compounds as claimed in claim 1 where in $R^6$ represents trifluoromethyl group in the 3-position, and one of $R^1$ to $R^5$ is other than hydrogen atom, A represents $$C_6H_5-\overset{|}{\underset{|}{C}H} \text{ group},$$

Q represents single bond or is alkylene group having at least 4 carbon atoms,

X represents sulphur atom, and

Z represents the group $$-\overset{/}{\underset{\backslash}{C}H}.$$

5. A compound selected from the group consisting of 3-{3-[4-(4-fluorophenyl)-1-piperazinyl]-propyl}-6,6-dimethyl-5,6-dihydrouracil hydrochloride hydrate; 3-[3-(4-phenyl-1-piperazinyl)-propyl]-6,6-dimethyl-5,6-dihydrouracil hydrochloride; 3-[3-(4-phenyl-1-piperazinyl)-propyl]-6,6-dimethyl-2-thio-5,6-dihydrouracil hydrochloride; 3-[3-(4-phenyl-1-piperazinyl)-propyl]-5,6-dimethyl-5,6-dihydrouracil hydrochloride; and 3-[2-(4-phenyl-1-piperazinyl)-ethyl]-6,6-dimethyl-2-thio-5,6-dihydrouracil hydrochloride and physiologically compatible acid addition salts thereof.

6. A pharmaceutical composition containing as active ingredients effective amounts for treating migraine at least one compound as claimed in claim 1 or a physiologically acceptable acid addition salt thereof in association with a pharmaceutical carrier or excipient.

7. A composition as claimed in claim 6 in the form of dosage units containing the active ingredient in an amount of from 0.1 to 50 mg.

* * * * *